United States Patent
Kassel et al.

(10) Patent No.: US 6,585,703 B1
(45) Date of Patent: Jul. 1, 2003

(54) DIVIDABLE INTRODUCER CATHETER AND POSITIVE-LOCK NEEDLE GUARD COMBINATION

(75) Inventors: Michael Kassel, Cambridge, MA (US); Mark Godfrey, Encinitas, CA (US); Scott Wells, Newburyport, MA (US)

(73) Assignee: Span-America Medical Systems, Inc., Greenville, SC (US)

( * ) Notice: Subject to any disclaimer, the term of this patent is extended or adjusted under 35 U.S.C. 154(b) by 130 days.

(21) Appl. No.: 09/626,237

(22) Filed: Jul. 26, 2000

Related U.S. Application Data

(60) Provisional application No. 60/146,015, filed on Jul. 28, 1999.

(51) Int. Cl.[7] .................................................. A61M 5/00
(52) U.S. Cl. ......................... 604/263; 604/192; 604/198
(58) Field of Search ................................ 604/263, 192, 604/198

(56) References Cited

U.S. PATENT DOCUMENTS

| | | | |
|---|---|---|---|
| 5,011,479 A | * 4/1991 | Le et al. ..................... 604/198 |
| 5,221,263 A | 6/1993 | Sinko et al. | |
| 5,693,022 A | * 12/1997 | Haynes ....................... 604/192 |
| 5,743,882 A | 4/1998 | Ronald | |
| 5,827,239 A | * 10/1998 | Dillon et al. ............... 604/263 |

* cited by examiner

*Primary Examiner*—Thomas Denion
*Assistant Examiner*—Theresa Trieu
(74) *Attorney, Agent, or Firm*—Gardner Carton & Douglas LLC

(57) ABSTRACT

An introducer catheter and needle guard assembly combination used with a peripherally inserted central catheter (PICC) is disclosed. The needle guard assembly includes a sliding needle hub for positively locking a needle in the needle guard assembly. The introducer catheter includes a tube portion and connector that can be divided into two halves. The needle guard assembly is secured to the introducer catheter and the extended needle and introducer catheter are inserted into the body of a patient. The needle and needle guard assembly can then be removed from the introducer catheter. A PICC line or other similar line can then be inserted through the catheter tube and into the patient. The tube portion and connector of the catheter are then divided into two halves so that the entire introducer catheter can be removed from the PICC line, or other similar line, that is inserted into the body of a patient.

19 Claims, 4 Drawing Sheets

DIVIDABLE INTRODUCER CATHETER AND POSITIVE-LOCK NEEDLE GUARD COMBINATION

This application claims the benefit of U.S. Provisional Application No. 60/146,015, filed Jul. 28, 1999.

FIELD OF THE INVENTION

This invention relates to peripherally inserted central and/or midline catheters lines and, more specifically, to a dividable catheter line introducer device that is fitted with a simple, very reliable and effective needle guard. The needle guard positively prevents hazardous needle sticks when the introducer needle has been retracted from the introducer catheter. After removal of the needle guard, a peripherally inserted central and/or midline catheter line is inserted through the catheter introducer into the patient, and the introducer catheter is divided into two halves that are removable from the line and patient.

BACKGROUND OF THE INVENTION

Intravenous catheters for the infusion of fluids into the veins of a patient are typically one of two general types. One type is the "through-the-needle" catheter wherein the catheter is threaded through the needle and into the vein of a patient. In the through-the-needle type catheter, the needle is not withdrawn from the patient upon placement of the catheter. The second type of catheter is the "over-the-needle" type. Upon insertion of the introducer catheter into a patient, the insertion needle is withdrawn leaving the catheter in the body.

Needle guards are known in the art, but are generally limited for use with short peripheral catheters. The introducer needle is mounted in the needle guard so that when the needle is removed from the catheter it is received into the needle guard. It is also known in the art to use positive-lock needle guards that positively lock the needle in the guard.

Short peripheral catheters are distinguishable from peripherally inserted central catheter ("PICC") lines in that PICC lines are inserted into the vascular system of the patient whereas short peripheral catheters are inserted into a vein of the patient. Not surprisingly, these different applications require different catheter structures and correspondingly different restrictions to the use of a needle guard on the introducer catheter.

In the use of a PICC line, a flexible catheter is introduced into the vascular system of a patient and subsequently manipulated to move the catheter through the vascular system of a patient to a desired location. Because the catheter must be moved upwardly through the vascular system, the catheter must be formed from a soft, biocompatible, pliable, and flexible material which is capable of winding through and extending through substantial lengths of the vascular system. It is not unusual for such catheters to extend from two to thirty inches or more through the vascular system of a patient. The insertion of the PICC line must also occur without causing trauma to the vascular system.

Because of the need to insert the PICC line catheter such long distances into the vascular system of a patient, the prior art devices tended to use through-the-needle catheter systems. In these through-the-needle catheter systems, after venous insertion, the needle or cannula is retained within the patient and the desired length of catheter is inserted through the cannula and into the vein of the patient. As will be apparent to those of ordinary skill in the art, in such applications, blood leakage is commonplace which exposes administrating personnel to substantial health risks, such as that associated with the AIDS virus, hepatitis, and other infectious diseases.

In view of these concerns, over-the-needle catheter systems have been recently introduced specifically adapted for PICC line applications. The use of over-the-needle catheter systems has made the use of needle guard that much more difficult.

In one prior art device, the insertion of a limited length (i.e., finite length) of catheter into a patient's vein is facilitated while permitting the needle to be withdrawn after the initial insertion via a stylet extending through the catheter and then stowed within a protective sheath to prevent accidental puncture and/or exposure. However, this prior art device is limited to the length of the catheter provided, necessitating the correct initial selection of catheter length. Further, this device has a relatively complex construction, is relatively costly to fabricate, increases the patient's cost, and is relatively complicated to use, requiring a significant amount of training and manipulative skill.

The short peripheral catheter, on the other hand, poses fewer barriers to the incorporation of a needle guard on the introducer catheter. The short peripheral catheter, like the syringe, employs only a needle stick to introduce a catheter that remains external to the patient's body. Therefore, the problems encountered where a catheter is inserted into the vascular system of a patient do not arise with the use of a short peripheral catheter. As such, the short peripheral catheter introducer relatively easily allows incorporation of a needle guard.

Today, PICC line introducers typically are "over-the-needle" catheters. Typically, the introducer needle used with PICC lines is not used with a needle guard assembly. The introducer needle is therefore exposed when removed from the body. The exposed introducer needle, after withdrawal from the catheter, exposes healthcare workers to the possibility of accidental needle sticks and all the associated risks of exposure to bloodborne pathogens during the subsequent handling and disposal process.

In an effort to overcome these problems, several devices have been disclosed in the prior art that attempt to provide some means of closing off, blocking, containing or otherwise preventing the needle tip in a syringe, catheter, or similar device from being exposed after withdrawal from a patient.

One such prior art system is disclosed in U.S. Pat. No. 5,000,740 to Ducharme et al. A catheter device is described with a safety needle guard that covers and protects the needle after use of the device. The device includes a semi-tubular needle housing containing a flash chamber with a hollow needle extending from the distal end of the flash chamber. A tubular needle guard concentrically fits and slides within the needle housing. The needle guard has a longitudinal slot through which the mounting base of the flash chamber passes as the guard slides within the housing. The top of the semi-tubular housing is open so that a user may access the top of the tubular needle guard with a finger to urge the needle guard to an extended position from the distal end of the housing and in a surrounding position about the needle. As the needle guard attains its fully extended position about the needle, it locks in place in the needle housing.

Another prior art system is disclosed in U.S. Pat. No. 5,000,736 to Kaufhold, Jr. et al. A medicinal syringe including a tubular plunger from which air has been evacuated and a seal member releasably attached on the distal end of the plunger. Upon application of a predetermined longitudinal axial force to the seal member, the attachment between the seal member and the plunger will rupture, releasing the seal member for movement within the plunger. The seal member when released will be forced by the differential pressure between the vacuum and the ambient air into the interior of the tubular plunger. The plunger is slidably disposed in a tubular barrel. A needle is disposed in a hub releasably attached within the distal end of the barrel. Upon application of a predetermined longitudinal axial force to the hub, the attachment between the hub and the barrel will rupture, releasing the hub for movement within the barrel. The hub when released will be forced by the pressure differential, along with the distal plunger seal member, into the interior of the tubular plunger, carrying the needle with it. The attachment between the hub and barrel is adapted to rupture prior to that between the seal member and plunger. Once drawn into the tubular plunger, the needle and hub will remain there indefinitely, thus eliminating accidental puncturing by the needle of a person in the vicinity of the syringe.

Bonaldo, U.S. Pat. No. 4,917,669, discloses a catheter inserter has an inserter housing with a flat base and a cannula housing disposed within the inserter housing with a cannula extending generally parallel to the inserter housing longitudinal axis. Stop means are disposed at each end of the inserter housing, locking means on the cannula housing selectively engage the stop means to lock the cannula housing in a first disposition in which the cannula extends outwardly from the inserter housing and in a second disposition in which the cannula is retracted within said inserter housing. The cannula housing has a passage in fluid communication with the cannula which, together with means on the inserter housing and cannula housing, permit the external viewing of flood passing into the fluid passage from the cannula.

Lasaitis et al, U.S. Pat. No. 5,102,394, discloses a catheter assembly for intravenous therapy includes a protective shield to protect health care personnel from inadvertent injury. The protective shield can be selectively positioned on the assembly to permit manipulation of a needle member of the assembly so that the needle member can be withdrawn from an associated tubular catheter member. After the needle member is withdrawn, it is received within the shield member, and is substantially enclosed therein so that the needle member can disposed of without injury to personnel.

Sircom, U.S. Pat. No. 5,458,658, discloses an automatic needle guard for intravenous catheter assemblies, which stores the insertion needle between the needle base and catheter hub, which attaches by positive engagement to the catheter hub, remains attached while the needle is withdrawn through the needle guard following insertion of the catheter, locks immovably to the needle shaft when the needle tip enters the body of the needle guard, then releases from the catheter hub, allowing the needle guard to be withdrawn along with the needle for safe disposal.

Another prior art system is disclosed in U.S. Pat. No. 5,279,591 to Simon. A protector guard housing is disclosed for a catheter type needle apparatus to prevent accidental needle puncture. The guard housing is initially positioned between the hub of the catheter and the handle of the needle which slidably extends through the catheter in a known manner. A detent mechanism initially retains the forward end of the guard to the catheter hub while needle supports within the guard permits the needle to axially move relative to the guard. When the needle is withdrawn from the catheter after site puncture, a resilient closure wall formed in the protector closes the protector's forward end while the needle's cutting end is simultaneously wedged into contact with friction retention material in the protector. The needle's cutting end is thus encapsulated within the protector when the detent mechanism releases the protector from the catheter.

Purdy et al., U.S. Pat. No. 5,215,528, discloses an assembly for introducing a catheter into a blood vessel is provided. The assembly includes a needle hub having a needle secured thereto. The needle includes an elongate shaft having a bevelled tip. A portion of the needle shaft adjacent to the tip has a relatively large outside diameter. The shaft diameter of this portion exceeds the diameter, of the shaft portion adjoining the tip and the diameter of the shaft portion extending between the enlarged shaft portion and the needle hub. A catheter is mounted over the shaft of the needle, and includes an inner surface which bears against the enlarged shaft portion. A substantially leak-proof seal is thereby provided between the catheter and the needle shaft. A needle tip cover is slidably mounted to the needle shaft and is engageable with the enlarged portion of the shaft to prevent its removal therefrom. The catheter is releasably mounted to the needle tip cover.

Steinman, U.S. Pat. No. 5,409,461, discloses a winged catheter introducer is disclosed. The catheter introducer has a catheter, a robe attached to the catheter and a winged intermediate member between the catheter and the robe. Within the catheter and the robe is a needle with a stylet attached to it. The stylet is attached to a hub which facilitates the pulling of the needle out of the catheter and through the robe. Attached to the robe is an adapter with a septum attached to it. The needle is provided with an opening extending from the needle wall to the needle lumen. A shielding device is provided which is attached to the adapter. The shielding device includes a needle container which is designed to trap the needle. A needle shield is provided inside the needle container. The needle is provided with an area of enlarged diameter. This area of enlarged diameter interacts with the needle shield when the needle is withdrawn from the catheter and robe and into the needle container. The needle shield is provided with an orifice through which the needle and stylet can fit but through which the area of enlarged diameter cannot pass. When the needle is withdrawn from the catheter and tube and into the needle container, it is trapped by the needle shield. The needle shield is also provided with a transverse wall which snaps over the point of the needle.

Haining, U.S. Pat. No. 5,176,650, discloses to protect against accidental needle prick a catheter and insertion device are provided wherein the needle is retractable within the device after insertion of the catheter. The device comprises a hollow barrel or tube of semi-rigid plastic material into which the needle can be retracted after use. The insertion needle is mounted on a carrier with the sharp end oriented toward an open insertion end of the barrel with the catheter snugly fit about the needle. A sliding tab is mounted to the carrier by an outwardly biased flexible member and extends through a longitudinal slot in the barrel. Near either end of the slot V notches are provided in the internal wall of the barrel to engage locking hubs on the sliding tab to releasably lock the carrier in either the exposed or retracted position. A flat catheter locking surface is provided at the insertion of the barrel with a reverse slope to allow the catheter flange to slide onto the flat surface and allow easy retraction of the needle without disturbing the inserted catheter.

Lemieux, U.S. Pat. No. 4,952,207, discloses an I.V. catheter is described, including a catheter and hub assembly and a needle and hub assembly. A needle guard, including a tubular distal portion and a split proximal flange, is located about the needle at the distal end of the needle hub. The needle includes a slot near the needle tip. As the needle assembly is withdrawn from the catheter, the needle guard slides along the needle until the split flange engages the needle slot, which locks the tubular distal portion of the guard over the needle tip.

Rossetti, U.S. Pat. No. 5,201,713, discloses one-way intravenous catheter assembly provided with a tubular needle guard slidable with respect to the needle housing, so as to completely cover the needle both before and after use, said needle housing comprising a substantially cylindrical central body with a flash chamber and a tapered front portion, to which the catheter needle is attached, and a peripheral finger gripping element, connected to the central body but extending around the tubular needle guard, the connection being provided by a connecting element which is slidable in a longitudinal slot of the tubular needle guard, the catheter assembly being further provided with a catheter tube or cannula mounted around the needle and provided with a hub for engagement with said tapered front portion of the needle housing.

Chang et al., U.S. Pat. No. 5,419,766, discloses a new catheter stick protector is described having a metal flap clip which snaps down into place to prevent return of the needle through the protector device once withdrawn. The device is small and received over the needle to provide an interface between the needle hub and the hub of a catheter like product. A sleeve of hydrophobic or fluid impermeable material is provided and attached at one end to the needle hub and at a second end to the tip protector. The length of the material is selected to hold the tip protector in a position just extending beyond the tip of the needle of a catheter inserter.

SUMMARY OF THE INVENTION

The present invention overcomes many of the deficiencies of the prior art by providing a introducer catheter and needle guard assembly combination that can be used for inserting a PICC line into a patient. The introducer catheter includes a first and second end and defines a fluid passageway between the first and second ends. The catheter includes a tube portion that terminates at the first end and is adapted for insertion into a body. The catheter also includes a connector hub for connecting to the needle guard assembly.

The needle guard assembly includes a housing and a slidable needle hub mounted within the housing and holding the needle. The needle hub and needle are slidable to an extended position wherein the needle extends through the passageway in the catheter and the sharp end or tip of the needle projects beyond the first end of the catheter. The needle hub and needle are also slidable to a retracted position wherein the needle is completely contained in the housing. The needle guard assembly may also include means for locking the needle hub and needle in the retracted position to prevent escape of the needle from the housing, or in the extended position to prevent movement of the needle within the body of a patient.

The catheter includes a connector for securing the catheter to the needle guard assembly. In an embodiment, the connector comprises a hub having a male luer for connection to a female luer on the needle guard assembly. While the use of male and female luer connectors is preferred, it will be understood that other suitable connectors could be used for connecting the catheter to the needle guard assembly.

In an embodiment, the catheter includes means for dividing or splitting the catheter into two halves. The catheter is divided or split in order to remove the catheter from a PICC line or other similar line inserted into the body of a patient. The dividing means preferably include at least one score line along the longitudinal length of the tube portion. In a preferred embodiment, the tube portion includes a pair of diametrically opposed score lines running along the longitudinal length of the tube to facilitate easy dividing and tearing of the tube portion catheter into two halves.

The dividing means also preferably include a means for dividing the connector hub into two portions. In a preferred embodiment, the connector hub is comprised of two halves that are held together by being fitted within a corresponding connector on the needle guard assembly. In an embodiment, the two halves of the hub connector include cooperating detents or a gasket to seat the connector hub. In an alternate embodiment, the connector hub is a one-piece assembly, and the connector hub includes a pair of diametrically opposed score lines to facilitate tearing of the connector hub into two halves. The connector hub and tube portion may be integral components or the tube portion may be swaged into a separate hub connector.

In an embodiment, the catheter includes a pair of arms that can be gripped by the user to facilitate dividing or splitting of the catheter. The arms includes flanges that are adhesively or otherwise secured to the two halves of the tube portion. The arms are bendable back and forth with respect to the tube portion to facilitate tearing of the tube portion into two halves. The arms are further adhesively or otherwise secured to the two halves of the connector hub of the catheter for facilitating separation of the connector hub into its respective two halves. The arms are preferably secured to the tube portion on opposite sides of the score line or score lines that run along the longitudinal length of the tube portion and secured to the connector hub on opposite sides of the separation line between the two halves of connector hub.

The present invention further includes a method for introducing a PICC line or other similar line into a body of a patient. In a preferred embodiment, the introducer catheter and needle guard assembly are preferably sold and provided in a connected one-piece assembly. Alternatively, the catheter and needle guard assembly can be sold unconnected and the user would first connect the needle guard assembly to the introducer catheter. In either embodiment, the needle hub and needle are then slid to the extended position so that the sharp end of the needle projects outwardly from the tube portion of the introducer catheter. The needle is then inserted into the body of a patient and the tube portion of the introducer catheter follows the needle into the body. After placement of the introducer catheter, the needle hub and needle are retracted so that the needle is completely contained in the housing. The needle guard can then be safely disconnected from the introducer catheter without danger of exposure to the sharp end of the needle. The needle guard assembly can then be discarded. The PICC line, or other similar line, is then introduced to the open end of the connector hub of the introducer catheter. The PICC line is slide through the tube portion of the introducer catheter and into a desired position within the body of a patient. After final placement of the PICC line, the healthcare worker can bend the arms on the introducer catheter back and forth with respect to the tube portion in order to initiate and facilitate tearing along the score lines on the tube portion to tear the introducer catheter into two halves. The two halves of the connector hub also easily separate because the needle guard assembly has been disconnected from the connector hub, or the connector hub can be torn into two halves if it is a single-piece assembly having a score line to facilitate tearing. Once the catheter is completely separated into two halves, the entire catheter can be easily removed from the PICC line and the body of the patient. The two halves of the introducer catheter can then be discarded, and just the PICC line, or other similar line, is left inserted in proper position into the body of the patient.

DETAILED DESCRIPTION OF THE INVENTION

Figure 1:
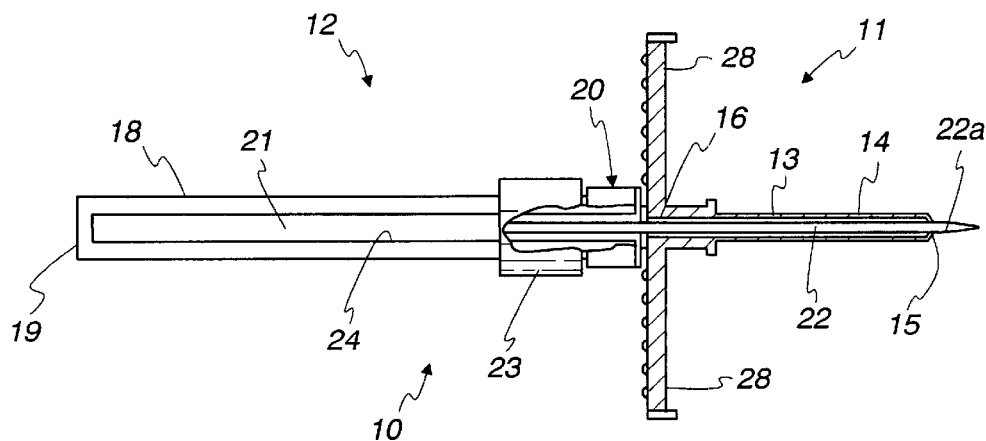
FIG. 1 is a schematic side view of the introducer catheter and needle guard combination of the present invention.
Figure 2:
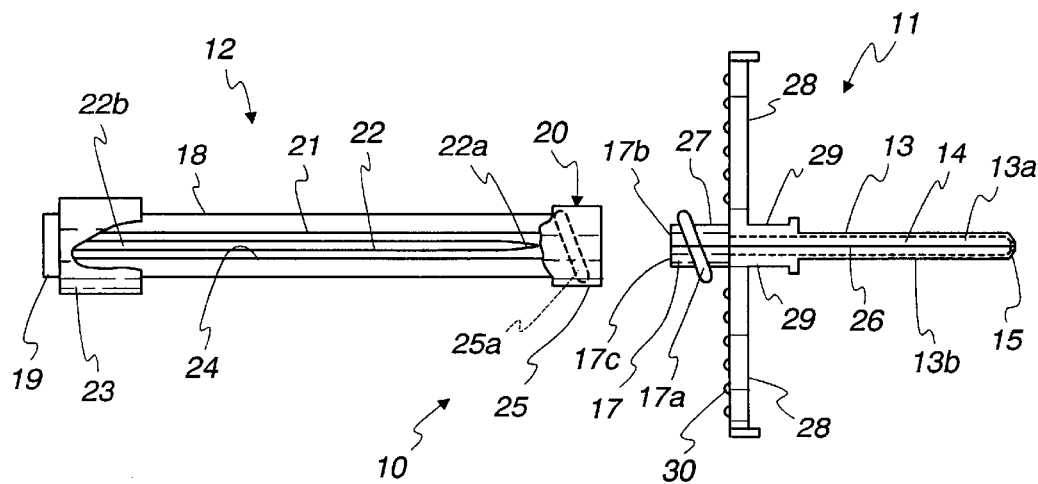
FIG. 2 is a schematic side view of the introducer catheter and needle guard combination of the present invention.

Referring to FIGS. 1 and 2, the present invention relates to an introducer catheter and needle guard combination 10 for use with a PICC line or similar line. The combination 10 includes an introducer catheter 11 and needle guard assembly 12. The catheter 11 includes a tube portion 13 defining a fluid passageway 14 extending between a first end 15 and second end 16 of the catheter 11. The first end 15 is shaped for insertion into a body. The second end 16 includes a connector for securing the catheter 11 to the needle guard assembly 12. In the embodiment given in the drawings, the connector takes the form of a connector hub 17 having a male luer 17a. However, other suitable fittings or connectors could be used.

The needle guard assembly 12 includes a housing 18 having a first end 19 and a second end 20. The housing 18 defines a hollow longitudinal chamber 21, and a needle 22 is slidably mounted within the hollow chamber 21 of housing 18. In particular, the needle 22 is mounted on a sliding needle hub 23 that travels in a pair of longitudinal slots 24 along the length of housing 18.

The housing 18 at its second end 20 includes a connector 25 for securing the needle guard assembly 12 to the catheter 11. In the embodiment given in the drawings, the second end 20 includes connector 25 having a female luer 25a for receiving the male luer 17a on connector hub 17. While luer fittings are believed to be preferred for securing the needle guard assembly 12 to the catheter 11, it would be understood by those skilled in the art that other suitable connectors could be used. Further, it will be understood that the male luer and female luer could be reversed with the male luer 17a being on connector 25 and the female luer 25a being within connector hub 17.

The needle 22 has a sharp end or tip 22a for insertion into the body, and the needle's opposing end 22b is mounted on the sliding needle hub 23. The needle 22 slides between an extended position shown in FIG. 1 wherein the needle 22 extends through the passageway 14 in catheter 11, and the sharp end or tip 22a of the needle 22 projects beyond the first end 15 of catheter 11. The sharp end or tip 22a of the needle 22 facilitates insertion of the catheter 11 into the body. After insertion, the sliding needle hub 23 and needle 22 are slidable to a retracted second position shown in FIG. 2 wherein the needle 22 is completely contained within housing 18 of needle guard 12. In the retracted position, the needle 22, and sharp end or tip 22a, are positioned inwardly of the second end 20 of housing 18. In a preferred embodiment, the sliding needle hub 23 can be locked into position at the retracted position to prevent movement of the needle 22 out of the hollow longitudinal chamber 21. The sliding needle hub can also be locked in the extended first position to prevent movement of the needle 22 in the body. An example of needle guard assemblies that can be used with the combination of the present invention are disclosed in co-owned U.S. Pat. Nos. 5,954,698 and 5,851,196, which are hereby incorporated by reference.

The catheter 11 preferably includes means for dividing the catheter 11 into two halves in order to remove catheter 11 from a line inserted through the catheter 11 and into a body. In the particular embodiment shown in FIG. 2, the tube portion 13 of catheter 11 includes a longitudinal score line 26, and the connector hub 17 includes a separation line 27. The tube portion 13 includes a diametrically opposed score line (not shown) on the other side of the tube portion 13 from scores line 26. Catheter 11 is preferably made of a material that facilitates tearing of the catheter 11 along the score line 26. The tube portion 13 of catheter 11 is preferably made of soft and pliable biocompatible material. As examples, the tube portion 13 can be made of soft urethane, Teflon, or silicone. These materials are safe for use in the body and also permit easy tearing of the tube portion 13 along the score line 26.

Figure 4:
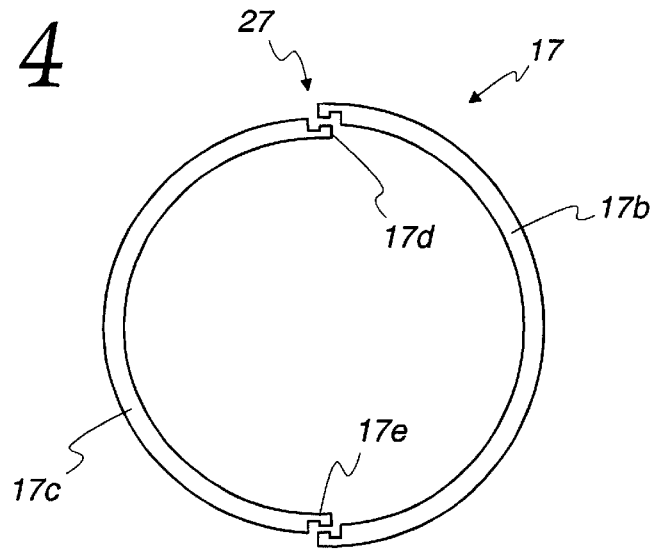
FIG. 4 is a schematic top view illustrating one embodiment of the connector hub of the introducer catheter of the combination of the present invention.

In an embodiment, the connector hub 17 is formed of two halves 17b and 17c on opposite sides of the separation line 27. As shown most clearly in FIG. 4, the two halves 17b and 17c include a slight overlapping portion at the separation line 27 and are held together by the connection with the needle guard assembly 12. In the particular embodiment shown in FIG. 4, the two halves 17b and 17c also include detents 17d and grooves 17e in order to form a tight seal between the two halves of connector hub 17 and to prevent leakage of blood therethrough. In the alternative, a gasket could be provided between the two halves 17b and 17c of connector hub 17, but it is believed that a pressure seal between the two halves is sufficient to prevent blood leakage therethrough.

In an alternate embodiment, the connector hub 17 can be a single-piece connector and the separation line 27 is formed by a score line or a pair of diametrically opposed score lines in the connector hub 17. Thus, when the user tears tube portion 13 into two halves, the user can also tear the connector hub 17 into two halves along the separation line 27 so that the entire introducer catheter 11 is separated into two halves.

In an embodiment, the connector hub 17 was made of polypropylene, and the tube portion 13 was a separate component swaged into the connector hub 17. While in that particular embodiment the connector hub 17 and tube portion 13 were separate components, it will be understood that the connector hub 17 and tube portion 13 could be integrally formed of the same material as long as the material is soft, pliable, biocompatable and facilitates, dividing or splitting of the connector hub 17 and tube portion 13 along score line 26 and separation line 27.

In the embodiment shown in the drawings, the catheter 11 further includes a pair of arms 28 that project perpendicularly to the tube portion 13 and connector hub 17 of catheter 11. As shown most clearly in FIG. 2, the arms 28 each include a flange 29 that is secured to tube portion 13 by an adhesive or other securement mechanism. The arms 28 and flanges 29 are secured to opposite halves 13a and 13b of tube portion 13 on opposite sides of the pair of diametrically opposed score lines 26. When it is desired to divide or split tube portion 13 into the two halves 13a and 13b, the arms 28 can be worked back and forth or bent with respect to tube portion 13 to initiate and facilitate, dividing or splitting of tube portion 13 along score lines 26.

With further reference to FIG. 2, the arms 28 are also secured to connector hub 17 by adhesive (not shown) or other suitable securement means. The arms 28 are secured to opposite halves 17b and 17c of connector hub 17, and are positioned on opposite sides of the separation line 27. In the embodiment where the connector connector hub 17 is formed of two separate halves that overlap, the arms 28 serve as handles for easier separation of the two halves 17b and 17c and obviate the need for any direct contact with the connector hub 17. In the embodiment in which the connector hub 17 is a single-piece component having a score line at the separation line 27, the arms 28 are used to facilitate initiation and propagation of a tear through the score line to separate connector hub 17 into its two halves 17b and 17c. The arms 28 can further include a plurality of nubs 30 to facilitate grasping of the arms 28 by healthcare worker during splitting of the catheter 11 into two halves.

The introducer catheter 11 and needle guard assembly 12 combination of the present invention is particularly advantageous for inserting a PICC line into a body. The method of using the combination 10 of the present invention to insert a PICC line or other similar line into a body is illustrated in FIGS. 3–7. While the method will generally be described in connection with inserting a PICC line into the body, it will be understood that the combination 10 and method of the present invention could also be used for introducing similar long lines into the body of a patient.

The introducer catheter 11 and needle guard assembly 12 combination are preferably provided and sold with the two components being connected together as shown in FIG. 1. The one-piece assembly is easier to handle and obviates the need for the healthcare worker to take the extra step of connecting the two components. While it is preferred that the two components be sold and provided in a connected condition as shown in FIG. 1, it will also be understood that the two components 11 and 12 could be packaged in an unconnected condition for connection by a healthcare worker.

Figure 3:
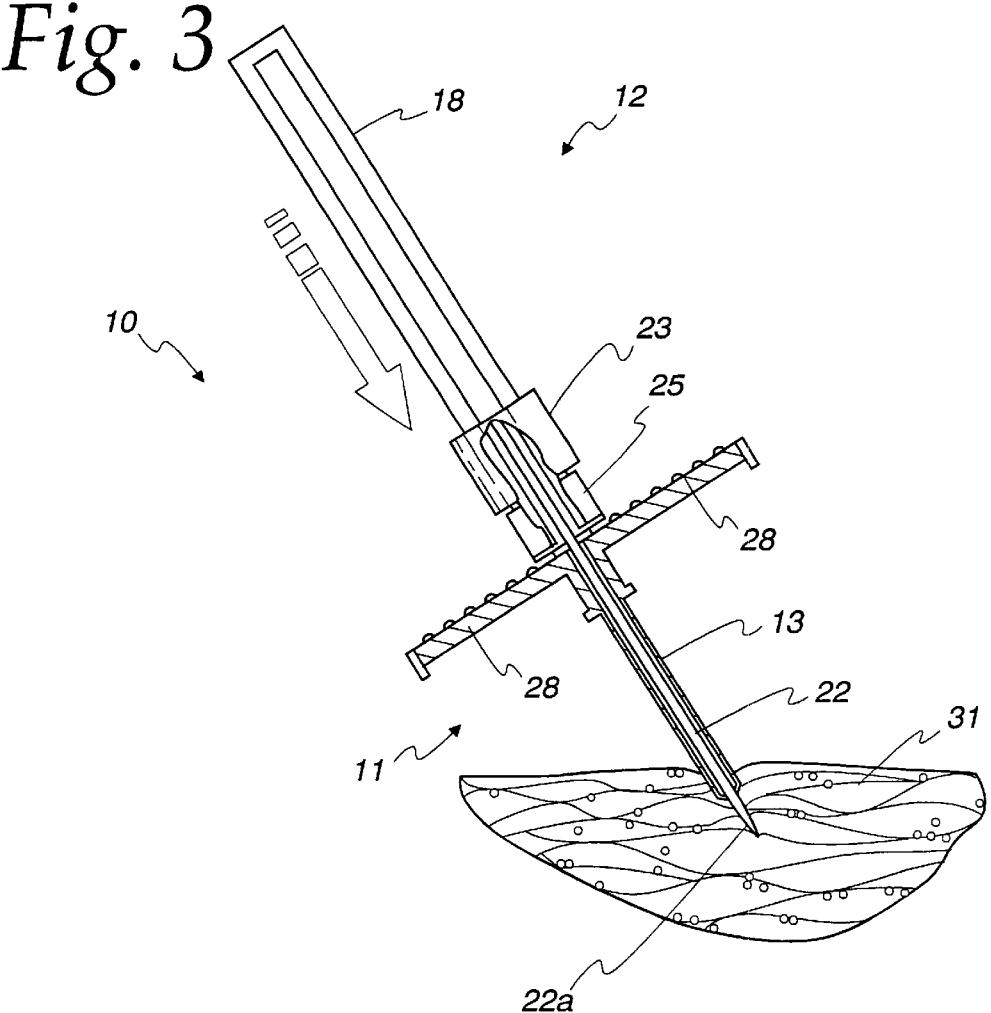
FIG. 3 is a schematic side view illustrating insertion of the introducer catheter and needle guard combination of the present invention into a body of a patient.

To insert the PICC line into a body, the connected introducer catheter 10 and needle guard assembly 12 are first inserted into the body as shown in FIG. 3. During insertion, the sliding needle hub 23 is positioned in the housing 18 in the extended position so that the needle 22 and sharp end or tip 22a extends out of the first end 15 of the catheter 11 for insertion into the body 31. The tube portion 13 of catheter 11 follows the needle 22 into the body and is positioned for the desired procedure. Once the catheter 11 is properly positioned within the body, the sliding needle hub 23 is moved into the retracted position so that the needle 22 is completely contained within the housing 18 as shown in FIG. 2. In a preferred embodiment, the sliding needle hub 23 is locked into the retracted position so that the needle 22 cannot be removed from the housing 18. The needle guard assembly 12 is then removed from the introducer catheter 11 by disconnecting the luer fittings 17a and 25a of connector hub 17 and connector 25.

Figure 5:
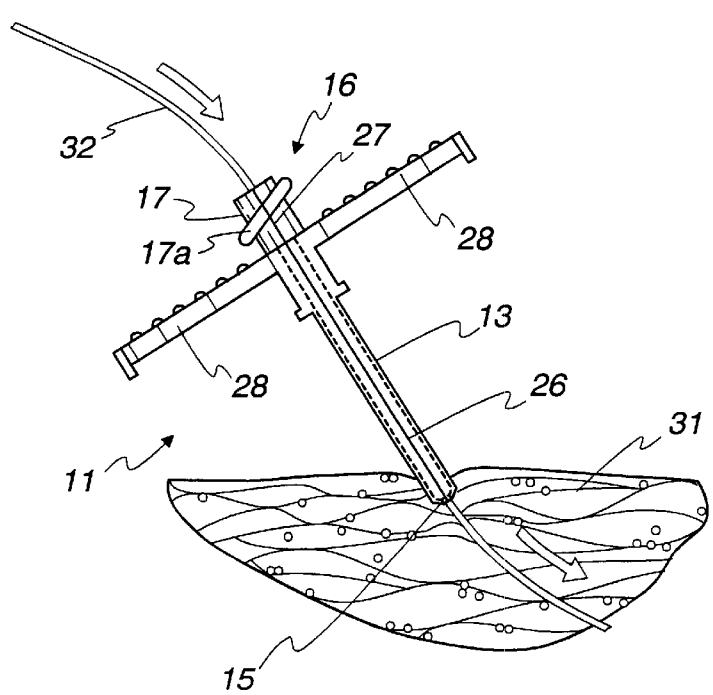
FIG. 5 is a schematic side view illustrating insertion of a PICC line through the introducer catheter of the present invention and into the body of patient.

Referring to FIG. 5, a PICC line 32 is inserted into the open second end 16 of introducer catheter 11 and pushed or extended to the desired location within the body 31. After proper placement of the PICC line 32, introducer catheter 11 is removed from the body. The introducer catheter 11 could be removed by sliding it along the PICC line 32 until catheter 11 is clear of the line 32. However, due to the length of such lines and normal connections to medical devices at the other end, it is believed to be preferable to use the catheter 11 having a dividing means shown in FIG. 5 for removal from the PICC line 32.

Figure 6:
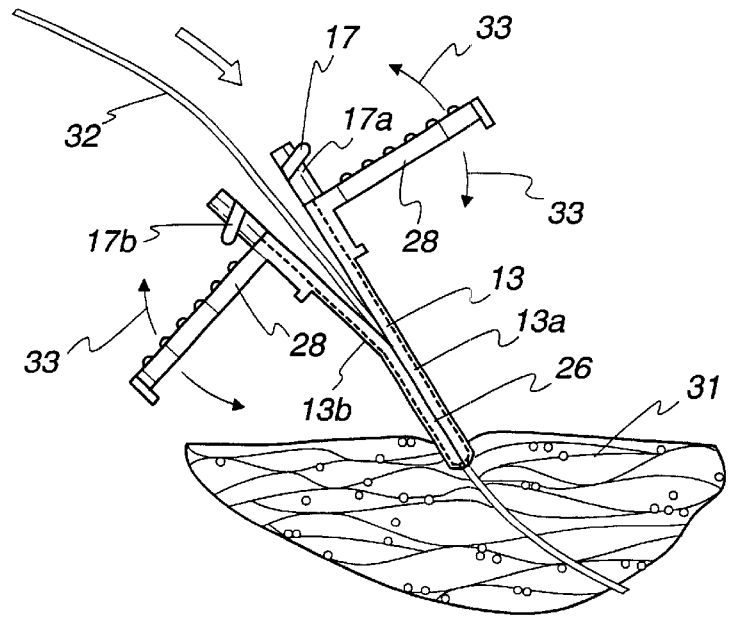
FIG. 6 is a schematic side view illustrating splitting of the introducer catheter of the present invention into two halves for removal from a PICC line and from the body of a patient.
Figure 7:
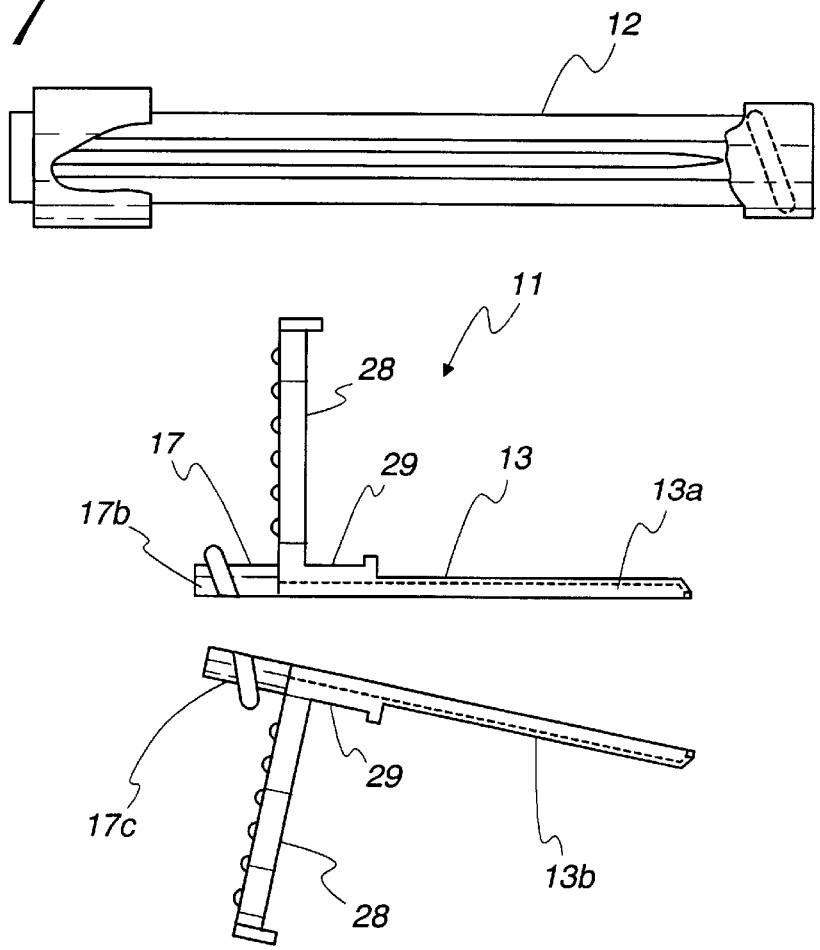
FIG. 7 is a schematic side view illustrating the needle assembly and introducer catheter split into two halves for disposal after use.
Figure 8:
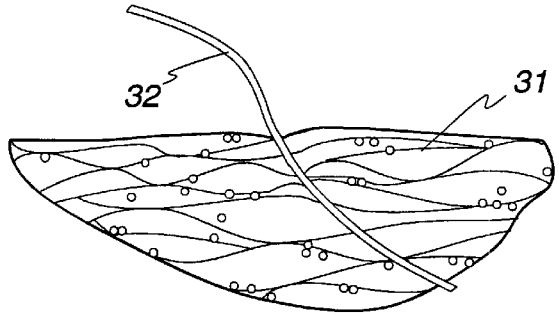
FIG. 8 is a schematic side view illustrating a PICC line inserted into the body of patient.

In particular, after proper positioning of the PICC line 32 through catheter 11, the healthcare worker can grasp handles 28 and work the handles back and forth with respect to tube portion 13 as represented by arrows 33 in FIG. 6. This working action causes tube portion 13 to be split into two halves 13a and 13b along score line 26. The working action also separates connector hub 17 along separation line 27 when the connector hub 17 is formed of two separate halves fitted together, or causes the connector hub 17 to split along a score line at separation line 27 when the connector hub 17 is a one-piece component. Once connector hub 17 and tube portion 13 are completely split into two halves, all of the components of catheter 11 can be easily removed from PICC line 32 and body 31. The complete removal of catheter leaves just the PICC line 32 extending into the body 31, as shown in FIG. 7. The used needle guard assembly 12 and used halves of catheter 11 as shown in FIG. 6 can then be safely discarded.

The introducer catheter and needle guard combination 10 of the present invention is particularly advantageous for use in inserting long lines, such a PICC line into the body. The needle guard assembly 12 assures safe handling and disposal of the needle 22. The dividable catheter 11 advantageously includes a dividable connector hub 17 for connection of the needle guard assembly 12 to permit their combined use. A dividing means on the connector hub 17, as well as the tube portion 13 of the catheter 11, then permit easy removal of the entire catheter 11 from the PICC line and body of the patient for safe and efficient disposal.

While this invention has been described with specific embodiments, many alternatives, modifications and variations will be apparent to those skilled in the art in light of the foregoing description. Accordingly, it is intended to include all such alternatives, modifications and variations set forth within the spirit and scope of the description.

We claim:

1. An introducer catheter and needle guard assembly combination comprising:
   a catheter having a first end and a second end and defining a fluid passageway between said first and second end, the catheter including a tube portion that terminates at the first end and is adapted for insertion into a body;
   the catheter further defining at least one score line extending from the first end to the second end and being adapted to facilitate separation of the catheter longitudinally into two separate halves;

a needle guard assembly including a housing, a sliding needle hub slidingly mounted within said housing, and a needle mounted on the needle hub, the needle being adapted to slide on the needle hub within the housing between an extended position wherein the needle projects out of the tube portion of the catheter and a retracted position wherein the needle is completely contained within said housing; and a connector disposed on the second end of the catheter and being adapted to connect to the needle guard assembly, the connector having a first half and second half, the hub adapted to hold the first half and the second half together.

2. The apparatus of claim 1, wherein a pair of arms are secured to the tube portion of the catheter and are bendable with respect to the tube portion to facilitate splitting of the tube portion.

3. The apparatus of claim 2, wherein the connector comprises a hub having one of a male and female luer, and the wings are secured to the hub to facilitate splitting of the hub.

4. The apparatus of claim 3, wherein the hub and tube portion are integral.

5. The apparatus of claim 1, wherein the tube portion of the catheter includes two diametrically opposed score lines.

6. The apparatus of claim 1, wherein the two halves of the connector each include a mating detent and groove for connecting the two halves of the connector together.

7. The apparatus of claim 1, wherein the needle hub is adapted to be locked into position at the extended position.

8. The apparatus of claim 1, wherein the needle hub is adapted to be locked into position at the retracted position.

9. The introducer catheter and needle guard assembly of claim 1, wherein the sliding needle hub is adapted to be locked into a retracted position so that the needle cannot be removed from the housing.

10. An introducer catheter assembly comprising:

a catheter having a tube portion with a first end and a second end, the first end being adapted for insertion into a body;

a connector on the second end of the tube portion for connecting to a needle guard assembly, the connector having a first half and second half;

means for holding the first half and the second half together; and means for dividing the tube portion and connector into two halves.

11. The catheter of claim 10 wherein the dividing means comprises at least one score line extending between the first and second ends of the tube portion.

12. The catheter of claim 10 wherein the connector comprises a hub having two halves fitted together.

13. The catheter of claim 10 further including a pair of opposed arms secured to opposite sides of the tube portion of the catheter and being bendable with respect to the tube portion to facilitate splitting or dividing of the tube portion of the catheter.

14. The catheter of claim 13 wherein the pair of wings are further secured to the connector and bending the wings further facilitates dividing of the connector.

15. A method of introducing a line into a body, said method comprising the steps of:

providing an introducer catheter having a connector and tube portion that can be separated into two halves and a needle guard assembly secured to the connector of the catheter, the needle guard assembly having a slidable needle contained therein;

sliding said slidable needle in the needle guard assembly to an extended position wherein a sharp end of the needle projects outwardly from the tube portion of the catheter;

inserting the sharp end of the needle and the tube portion of the catheter into a body;

sliding the needle to a retracted position wherein the needle is withdrawn from said body and the catheter and is completely contained within the needle guard assembly;

detaching the needle guard assembly from the catheter;

inserting a line into the catheter and into the body; and dividing the tube portion and connector of the catheter into two halves and removing the catheter from said body.

16. The method of claim 15 wherein said step of dividing said catheter includes grasping at least one arm on the catheter and tearing the catheter along its length.

17. The method of claim 15 wherein said step of dividing said catheter includes splitting said tube portion along at least one score line along the length of the tube portion.

18. The method of claim 15 wherein said step of dividing said catheter includes separating two halves of the connector that are fitted together.

19. The method of claims 15 wherein said step of inserting said line into the body includes inserting a PICC line into said body.

* * * * *